US007553336B2

(12) United States Patent
Speckbacher et al.

(10) Patent No.: US 7,553,336 B2
(45) Date of Patent: *Jun. 30, 2009

(54) BRIGHTENING DIRECT DYES FOR KERATIN FIBERS AND COLORANTS CONTAINING THESE COMPOUNDS

(75) Inventors: Markus Speckbacher, Aschaffenburg (DE); Hans-Juergen Braun, Ueberstorf (CH)

(73) Assignee: Wella AG, Darmstadt (DE)

(*) Notice: Subject to any disclaimer, the term of this patent is extended or adjusted under 35 U.S.C. 154(b) by 432 days.

This patent is subject to a terminal disclaimer.

(21) Appl. No.: 10/585,032

(22) PCT Filed: Oct. 26, 2004

(86) PCT No.: PCT/EP2004/012077

§ 371 (c)(1),
(2), (4) Date: Jun. 29, 2006

(87) PCT Pub. No.: WO2005/074872

PCT Pub. Date: Aug. 18, 2005

(65) Prior Publication Data

US 2007/0119000 A1 May 31, 2007

(30) Foreign Application Priority Data

Feb. 7, 2004 (DE) .................. 10 2004 006 141

(51) Int. Cl.
*A61Q 5/10* (2006.01)
*C07D 221/04* (2006.01)
(52) U.S. Cl. ............... 8/405; 8/407; 8/426; 8/552; 8/568; 8/576; 546/99
(58) Field of Classification Search ............. 8/405, 8/407, 426, 552, 568, 576; 546/99
See application file for complete search history.

(56) References Cited

U.S. PATENT DOCUMENTS 4,927,729 A     5/1990  Harnisch et al.
5,292,881 A     3/1994  Berneth et al.
5,370,959 A  *  12/1994 Hagiwara et al. ...... 430/123.51
6,391,062 B1 *  5/2002  Vandenbossche et al. ... 8/405

FOREIGN PATENT DOCUMENTS

| CH | 520 677   | 5/1972  |
|----|-----------|---------|
| DE | 2 147 706 | 3/1973  |
| DE | 23 41 289 | 3/1975  |
| DE | 24 23 547 | 12/1975 |
| DE | 26 25 410 | 12/1977 |
| DE | 26 50 226 | 5/1978  |
| DE | 29 50 035 | 7/1981  |
| EP | 0 501 249 | 9/1992  |
| FR | 2 072 126 | 9/1971  |
| GB | 1 585 643 | 3/1981  |
| GB | 1 585 668 | 3/1981  |
| JP | 1 202760  | 8/1989  |

OTHER PUBLICATIONS

STIC Search Report dated Oct. 23, 2008.*

* cited by examiner

*Primary Examiner*—Eisa B Elhilo
(74) *Attorney, Agent, or Firm*—Michael J. Striker

(57) ABSTRACT

The present invention has for an object brightening cationic naphthalene dyes of formula (I) and colorants for keratin fibers, particularly human hair, containing these compounds (I)

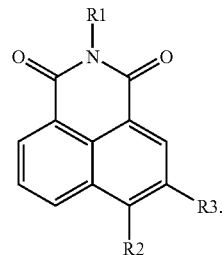

11 Claims, No Drawings

BRIGHTENING DIRECT DYES FOR KERATIN FIBERS AND COLORANTS CONTAINING THESE COMPOUNDS

CROSS-REFERENCE TO RELATED APPLICATIONS

This is the US National Stage of PCT/EP04/12077, filed on 26 Oct. 2004, and claims priority under 35 U.S.C. 119(a)-(d) to German Patent Application No. 10 2004 006 141.6, filed 7 Feb. 2004.

The present invention has for an object brightening naphthalene dyes and colorants for fibers, particularly keratin fibers, for example human hair, containing these compounds.

The brightening of pigmented keratin fibers (for example, brown hair) is usually done with chemical oxidants which destroy the natural pigments. Because this always results in damage to the keratin fibers, a great need exists for brightening colorants that are effective without chemical oxidants. The object of the present invention therefore is to provide dyes for brighter coloring of keratin fibers, particularly human hair, and which do not require chemical oxidants.

Surprisingly, we have now found that certain cationic naphthalene dyes of general formula (I), as direct dyes in dye compositions devoid of chemical oxidants, for example hydrogen peroxide and/or persulfates, can be applied to keratin fibers in a very gentle manner so that after the treatment with these dyes the hair shows a very natural brightening.

Hence, the present invention has for an object cationic naphthalene derivatives of general formula (I)

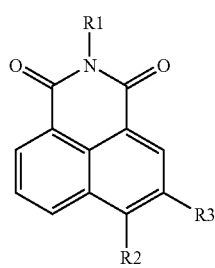
(I)

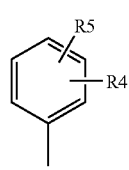
(II)

wherein $R_1$ stands for a hydrogen atom, an aliphatic alkyl group which can be linear or branched, unsubstituted or substituted with one or more hydroxyl groups or with cationic groups of type $B^+$ defined in the following, or it stands for an aromatic group of general formula (II) or (III);

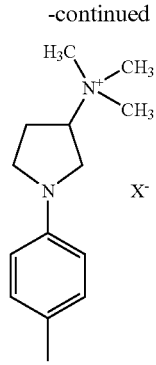
(III)

$R_2$ and $R_3$ independently of each other stand for hydrogen, $-NO_2$ or an $-N=C-R_6R_7$ group;

$R_4$ and $R_5$ can be equal or different and stand for hydrogen, an amino group, $(C_1-C_6)$-alkylamino group, a $(C_1-C_6)$-N,N-dialkylamino group, a $(C_1-C_6)$-N,N-(dihydroxyalkyl)amino group, fluorine, chlorine, bromine, iodine, a cyano group, a $(C_1-C_6)$-alkylcyano group, a methoxymethyl group, a tert.butyl group, an isopropyl group, a $(C_1-C_6)$-alkyl group, a $(C_1-C_6)$-alkyloxy group, a $(C_1-C_6)$-hydroxyalkyl group, a $(C_1-C_6)$-hydroxyalkyloxy group, a $(C_1-C_6)$-alkylcarboxylic acid group, a $(C_1-C_6)$-alkylcarboxylate ester group, a $(C_1-C_6)$-alkylcarboxamide group, a $(C_1-C_6)$-alkylsulfonic acid group, a $(C_1-C_6)$-alkylsulfonate ester group, a $(C_1-C_6)$-alkylsulfonamide group, a phenyl group or an -(L)-$B^+$ group;

$R_6$ stands for hydrogen, a $(C_1-C_6)$-alkylamino group, a $(C_1-C_6)$-N,N-dialkylamino group, a $(C_1-C_6)$-alkylcyano group, a methoxymethyl group, a tert.butyl group, an isopropyl group, a $(C_1-C_6)$-alkyl group, a $(C_1-C_6)$-alkyloxy group, a $(C_1-C_6)$-hydroxyalkyl group, a $(C_1-C_6)$-alkylcarboxylic acid group, a $(C_1-C_6)$-alkylcarboxylate ester group, a $(C_1-C_6)$-alkylcarboxamide group, a $(C_1-C_6)$-alkylsulfonic acid group, a $(C_1-C_6)$-alkylsulfonate ester group, a $(C_1-C_6)$-alkylsulfonamide group, a phenyl group or an -(L)-$B^+$ group;

$R_7$ stands for a group of formula (IV), (V), (VI) or (VII);

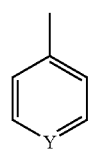
(IV)

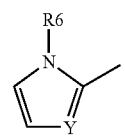
(V)

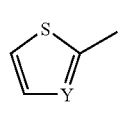
(VI)

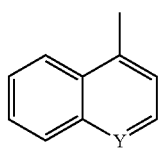
(VII)

L stands for a ($C_1$-$C_6$)-alkylene group;

$B^+$ stands for an aromatic, heterocyclic quaternary ammonium compound—preferably a quaternary compound of N-methylimidazole, N-allylimidazole, 2-ethylimidazole, 1,2-dimethylimidazole; a quaternary compound of pyridine, 4-dimethylaminopyridine, pyrimidine, pyrazole, N-methylpyrazole or quinoline; a nonaromatic heterocyclic quaternary ammonium compound—preferably a quaternary compound of N-methylmorpholine, N-ethylmorpholine or 1-methylpiperidine; a quaternary alkylammonium or arylammonium compound of formula $NR_aR_bR_c$ wherein $R_a$, $R_b$ and $R_c$ independently of each other denote a benzyl group, a phenyl group or a ($C_1$-$C_6$)-alkyl group—particularly a methyl, ethyl, propyl, isopropyl or butyl group, and the aforesaid alkyl groups possibly are unsubstituted or substituted with one or more hydroxyl groups or amino groups; or a quaternary phosphonium group, for example a tributylphosphonium group, but particularly a trimethylammonium group or a triethylammonium group;

Y stands for a nitrogen atom or preferably a quaternary nitrogen atom substituted with branched or linear ($C_1$-$C_6$)-alkyl, ($C_2$-$C_4$)-hydroxyalkyl or ($C_4$-$C_6$)-polyhydroxyalkyl groups; and $X^-$ denotes an anion, for example a halogen ion ($F^-$, $Cl^-$, $Br^-$, $I^-$), a sulfate, phosphate, hydrogen phosphate, oxalate, formate, acetate, citrate, tartrate, malonate or pyruvate ion and particularly a chloride, bromide or methylsulfate anion;

provided that at least one of the $R_1$ to $R_3$ groups is a cationic group.

Suitable naphthalene derivatives of general formula (I) are, for example, the following: 4-{(E)-[(1,3-diketo-2,3-dihydro-1H-benzo[de]isoquinolin-6-yl)imino]methyl}-1-(2-hydroxyethyl)pyridinium bromide, 4-{[(E)-[2-{4-[ethyl(2-hydroxyethyl)amino]phenyl}-(1,3-diketo-2,3-dihydro-1H-benzo[de]isoquinolin-6-yl)imino]methyl}-1-methylpyridinium methylsulfate, 1-(2-hydroxyethyl)4-{(E)-(2-methyl-1,3-diketo-2,3-dihydro-1H-benzo[de]isoquinolin-6-yl)iminomethyl}pyridinium bromide, 1-methyl-4-{(E)-[(2-methyl-1,3-diketo-2,3-dihydro-1H-benzo[de]isoquinolin-6-yl)imino]methyl}pyridinium methylsulfate, 1-methyl-4-{(E)-[(2-methyl-1,3-diketo-2,3-dihydro-1H-benzo[de]isoquinolin -6-yl)imino]methyl}quinolinium methylsulfate, 4-[(E)-({2-[2-hydroxy-1-(hydroxymethyl)ethyl]-1,3-diketo-2,3-dihydro-1H-benzo[de]isoquinolin-6-yl}imino)methylpyridinium methylsulfate, 4-((E)-{[2-(3,4-dichlorophenyl)-1,3-diketo-2,3-dihydro-1H-benzo[de]isoquinolin -6-yl]imino}methyl)-1-(2-hydroxyethyl)pyridinium bromide and 2-[(E)-({2-[2-hydroxy-1-(hydroxymethyl)ethyl]-1,3-diketo-2,3-dihydro-1H-benzo[de]isoquinolin-6-yl}imino)methyl]-3-methyl-1,3-thiazol-3-ium methylsulfate.

Preferred compounds of general formula (I) are 4-{[(E)-[1,3-diketo-2,3-dihydro-1H-benzo[de]isoquinolin -6-yl)imino]methyl}-1-(2-hydroxyethyl)pyridinium bromide, 1-(2-hydroxyethyl)4{(E)-[2-methyl-1,3-diketo-2,3-dihydro-1H-benzo[de]isoquinolin-6-yl)iminomethyl}pyridinium bromide, 1-methyl-4-{(E)-[(2-methyl-1,3-diketo-2,3-dihydro-1H-benzo[de]isoquinolin -6-yl)imino] methyl}pyridinium methylsulfate and 1-methyl-4-{(E)-[2-methyl-1,3-diketo-2,3-dihydro-1H-benzo[de]isoquinolin -6-yl)imino]methyl}quinolinium methylsulfate.

The naphthalene derivatives of general formula (I) can be obtained by standard methods from commercially available or readily prepared components [for example naphthalene precursors of formula (VIII)]. For example, the following compounds can be used as naphthalene precursors of general formula (VIII) wherein E stands for an N—H group or an oxygen atom:

4-aminonaphthalene-1,8-dicarboximide, 4-nitronaphthalene-1,8-dicarboxylic anhydride or 3-nitronaphthalene-1,8-dicarboxylic anhydride.

By a condensation reaction at elevated temperature in an appropriate solvent, for example glacial acetic acid or molten imidazole, the desired naphthalene starting compound of general formula (VIII) can be reacted with a primary aliphatic or aromatic amine according to Scheme 1 to prepare the corresponding imide.

Scheme 1

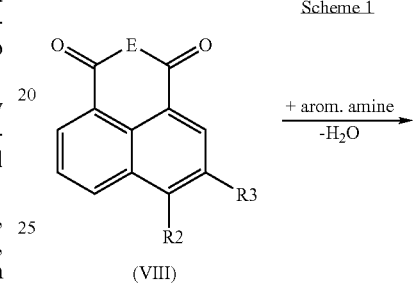

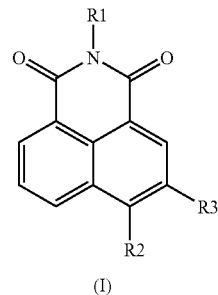

(I)

A cationic group can be introduced either according to Scheme 2

Scheme 2

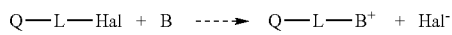

by subjecting, in a dipolar aprotic solvent, compounds of general formula Q-L-Hal [wherein group Q stands for any dye, L stands for a ($C_1$-$C_6$)-alkyl group and Hal stands for chlorine, bromine or iodine] to nucleophilic substitution with compounds of type B [wherein B stands for an aromatic, heterocyclic compound—preferably N-methylimidazole, N-allylimidazole, 2-ethylimidazole, 1,2-dimethylimidazole, pyridine, 4-dimethylaminopyridine, pyrimidine, pyrazole, N-methylpyrazole or quinoline; a nonaromatic heterocyclic compound—in particular N-methylmorpholine, N-ethylmorpholine or 1-methylpiperidine; an alkyl or aryl compound of formula $NR_aR_bR_c$, wherein $R_a$, $R_b$ and $R_c$ independently of each other denote a benzyl group, a phenyl group, or a ($C_1$-$C_6$)-alkyl group—particularly a methyl, ethyl, propyl, isopropyl or tert.butyl group, the said alkyl groups possibly being unsubstituted or substituted with one or more hydroxyl groups or amino groups; or a tertiary phosphor-organic group ("tertiary phosphine"), and particularly a trimethylamino group, triethylamino group or tributylamino group], or according to Scheme 3

Scheme 3

by quaternization of heterocyclic nitrogen atoms with alkylating agents of general formula X-R10 [wherein X stands for chlorine, bromine, iodine or methylsulfate and R10 stands for a ($C_1$-$C_6$)-alkyl group, a ($C_1$-$C_3$)-hydroxyalkyl group or a ($C_4$-$C_6$)-polyhydroxyalkyl group].

With the naphthalene derivatives of general formula (I) it is possible to achieve a uniformly brightening coloration of fibrous materials, particularly human hair, with unusually good resistance to light, perspiration and shampooing. Even under mild conditions, the naphthalene derivatives of general formula (I) of the invention bring about a very natural brightening, or a brighter coloration, of keratin fibers, for example wool, furs or other fibrous materials and particularly hair.

Hence, the present invention has for an another object an agent for dyeing and particularly for dyeing and brightening keratin fibers, particularly human hair, characterized in that it contains at least one naphthalene derivative of general formula (I).

The colorant of the invention contains the naphthalene derivatives of general formula (I) preferably in an amount from 0.01 to 10 weight percent and particularly from 0.1 to 8 weight percent.

Furthermore, the colorant of the invention can contain all common additives known to be used in such preparations, for example perfume oils, complexing agents, waxes, preservatives, thickeners, alginates, guar gum, hair-care substances, for example cationic polymers or lanolin derivatives, or anionic, nonionic, amphoteric or cationic surface-active substances. Preferably used are amphoteric or nonionic surface-active substances, for example betaine surfactants, propionates and glycinates, for example cocoamphoglycinates or cocoamphodiglycinates, ethoxylated surfactants with 1 to 1000 ethylene oxide units, preferably with 1 to 300 ethylene oxide units, for example glyceride alkoxylates with, for example, 25 ethylene oxide units, ethoxylated castor oil, polyethylene glycol amides, ethoxylated alcohols, ethoxylated fatty alcohols (fatty alcohol alkoxylates) and ethoxylated sugar esters of fatty acids, particularly ethoxylated sorbitan fatty acid esters. The afore-said constituents are used in amounts commonly employed for such purposes, for example the surface-active substances at a concentration of 0.1 to 30 weight percent, and the hair-care agents in an amount from 0.1 to 5 weight percent.

The colorant of the invention, particularly when it is a hair colorant, can be in the form of an aqueous or aqueous-alcoholic solution or a cream, gel, emulsion or aerosol foam. The hair colorant can be in the form of a one-component preparation or in the form of a multicomponent preparation, for example in the form of a two-component preparation in which the naphthalene derivative of general formula (I) is packaged separately from the other constituents, and the ready-to-use hair colorant is prepared just before use by mixing the two components.

The colorant of the invention has a pH of about 2 to 10, preferably about 5 to 10 and particularly a neutral pH of about 7 to 10. Both organic and inorganic acids and bases are suitable for pH adjustment. Suitable acids are, in particular, α-hydroxycarboxylic acids, for example glycolic acid, lactic acid, tartaric acid, citric acid or malic acid, ascorbic acid, glucuronolactone, acetic acid, hydrochloric acid or phosphoric acid as well as mixtures of these acids. Suitable bases are, in particular, sodium carbonate, sodium hydrogen carbonate, alkanolamines, for example monoethanolamine or triethanolamine, ammonia, aminomethylpropanol and sodium hydroxide.

The colorant of the invention is used without addition of a chemical oxidant.

As a rule, the colorant of the invention is used by applying to the fibers an amount sufficient for the dyeing, usually about 30 to 120 grams depending on the length of the fibers, after which the colorant is allowed to act at about 15 to 45° C. for about 1 to 60 minutes and preferably for 5 to 30 minutes. The fibers are then thoroughly rinsed with water, optionally washed with a shampoo and then dried.

Moreover, the afore-described colorant can contain natural or synthetic polymers or modified polymers of natural origin commonly used in cosmetic agents whereby a fixing and the dyeing of the hair are achieved at the same time. Such agents are generally referred to as tint fixatives or dye fixatives.

Synthetic polymers that are known to be used for this purpose in the cosmetic field are, for example, polyvinylpyrrolidone, polyvinyl acetate and polyvinyl alcohol, or polyacrylate compounds such as polyacrylic acid or polymethacrylic acid, basic polymers of esters of polyacrylic acid, polymethacrylic acid and aminoalcohols, for example the salts or quaternization products thereof, polyacrylonitrile and polyvinyl acetate, as well as the copolymers of such compounds, for example polyvinylpyrrolidone-vinyl acetate. Natural polymers or modified natural polymers that are suitable for such use are, for example, chitosan (deacetylated chitin) or chitosan derivatives.

The afore-said polymers can be contained in the colorant of the invention in amounts commonly employed in such cosmetic agents, particularly in an amount from about 1 to 5 weight percent. The pH of the tint fixative or dye fixative of the invention is preferably about 6 to 9.

The colorant additionally providing hair fixing is used in the known and usual manner by moistening the hair with the fixing agent, arranging (styling) the hair into a hairdo and then drying.

The colorant of the invention imparts to keratin fibers (for example human hair, wool or furs) an outstanding, uniform and very durable brightening coloration of without appreciably staining the skin or the scalp. The said coloration can withstand five or more hair washings without showing any noteworthy change in color.

The following examples will explain the subject matter of the invention in greater detail without limiting it to the examples.

EXAMPLES

Example 1

Preparation of 4-{(E)-[(1,3-diketo-2,3-dihydro-1H-benzo[de]isoquinolin-6-yl)imino]methyl}-1-(2-hydroxyethyl)pyridinium bromide Step 1: Preparation of 6-{[(E)-4-pyridinylmethylidene]amino}-1H-benzo[de]isoquinolin-1,3-(2H)-dione 3 g (14.13 mmol) of 4-aminonaphthalene-1,8-dicarboximide and 7.56 g (70.65 mmol) of 4-pyridinecarboxaldehyde in 180 mL of a 2:1 mixture of concentrated sulfuric acid and glacial acetic acid were stirred at 80° C. for 2 hours. The mixture was then poured onto ice and slowly neutralized or adjusted to a slightly alkaline pH (pH=about 8) with NaOH. The resulting precipitate was suction-filtered, washed with copious amounts of water and then dried under vacuum.

Yield: 2.28 g (54% of the theoretical), lustrous yellow powder $^1$H-NMR($d_6$-DMSO/300 MHz): δ=6.46 (s, 1H); 7.52-7.56 (m, 2H, aromatic); 7.20 (d, J=5.7 Hz, 2H, pyridyl); 8.38 (m, 1H, aromatic); 8.65 (d, J=5.7 Hz, 2H, pyridyl), 8.71-8.73 (m, 2H, aromatic); 11.41 (s, 1H, N—H).

Step 2; Preparation of 4-{(E)-[(1,3-diketo-2,3-dihydro-1H-benzo[de]isoquinolin-6-yl)imino]-methyl}-1(2-hydroxyethyl)pyridinium bromide 2.34 g (18.75 mmol) of bromoethanol was added dropwise to a solution of 1.13 g (3.75 mmol) of 6-{[(E)-4-pyridinylmethylidene]amino}-1H-benzo[de]isoquinolin-1,3(2H)-dione in 60 mL of acetonitrile or acetone and the solution was then heated at reflux for 1 hour. After concentration to about ⅓ of the amount of solvent and cooling to room temperature, the resulting precipitate was suction-filtered, washed with ethyl acetate and dried under vacuum.

Yield: 0.59 g (37% of the theoretical), dark-yellow powder $^1$H-NMR ($d_6$-DMSO/300 MHz): δ=3.58 (t, J=13.5 Hz, ethyl); 4.01 (t, J=13.5 Hz, 2H, ethyl); 6.45 (s, 1H); 7.54-7.58 (m. 2H, aromatic); 7.19 (d, J=5.8 Hz, 2H, pyridyl); 8.40 (m, 1H, aromatic); 8.63 (d, J=5.8 Hz, 2H, pyridyl); 8.72-8.75 (m, 2H, aromatic); 11.39 (s, 1H, N—H).

Example 2

Hair Colorant (Without Oxidant)

2.5 mmol of 4-{(E)-[(1,3-diketo-2,3-dihydro-1H-benzo[de]isoquinolin-6-yl)-imino]methyl}-1-1(2-hydroxyethyl)pyridinium bromide [=naphthalene derivative of general formula (I)]
5.0 g of ethanol
4.0 g of decylpolyglucose
0.2 g of disodium ethylenediaminetetraacetate hydrate
to 100.0 g water The dye solution was adjusted to pH 7 to 10 by addition of ammonia.

The hair was dyed by applying to the hair an amount of colorant sufficient for hair dyeing. After an exposure time of 30 minutes at 40° C., the hair was rinsed with lukewarm water and dried.

| Coloring result: | |
| --- | --- |
| Natural hair (before dyeing): | After dyeing: |
| L = 29.34 | L = 33.72 |
| a = +5.32 | a = +5.02 |
| b = +10.34 | b = +16.67 |

Result: The hair showed a natural brightening compared to the undyed hair.

The L*a*b* test data determined in the present examples were obtained with a Chromameter II instrument supplied by Minolta. L stands for brightness (namely the lower the L-value the darker is the color), whereas the a-value is a measure of the red content (namely the higher the a-value the higher is the red content). The b-value is a measure of the blue content of the color, said content being the higher the more negative is the b-value.

Unless otherwise indicated, all percentages given in the present patent application are by weight.

What is claimed is:

1. A cationic naphthalene derivative selected from the group consisting of 4-{(E)-[(1,3-diketo-2,3-dihydro-1H-benzo[de]isoquinolin-6-yl)imino]methyl}-1-(2-hydroxyethyl)pyridinium bromide, 4-{[(E)-[2-{4-[ethyl(2-hydroxyethyl)amino]phenyl}-(1,3-diketo-2,3-dihydro-1H-benzo[de]isoquinolin-6-yl)imino]methyl}-1-methylpyridinium methylsulfate, 1-(2-hydroxyethyl)-4-{(E)-(2-methyl-1,3-diketo-2,3-dihydro-1H-benzo[de]isoquinolin-6-yl)iminomethyl}pyridinium bromide, 1-methyl-4-{(E)-[(2-methyl-1,3-diketo-2,3-dihydro-1H-benzo[de]isoquinolin-6-yl)imino]methyl}pyridinium methylsulfate, 1-methyl-4-{(E)-[(2-methyl-1,3-diketo-2,3-dihydro-1H-benzo[de]isoquinolin-6-yl)imino]methyl}quinolinium methylsulfate, 4-[(E)-({2-[2-hydroxy-1-(hydroxymethyl)ethyl]-1,3-diketo-2,3-dihydro-1H-benzo[de]isoquinolin-6-yl}imino)methylpyridinium methylsulfate, 4-((E)-{[2-(3,4-dichlorophenyl)-1,3-diketo-2,3-dihydro-1 H-benzo[de]isoquinolin-6-yl]imino}methyl)-1-(2-hydroxyethyl)pyridinium bromide and 2-[(E)-({2-[2-hydroxy-1-(hydroxymethyl)ethyl]-1,3-diketo-2,3-dihydro-1H-benzo[de]isoquinolin-6-yl}imino)methyl]-3-methyl-1,3-thiazol-3-ium methylsulfate.

2. The cationic naphthalene derivative as defined in claim 1, selected from the group consisting of 4-{[(E)-[1,3-diketo-2,3-dihydro-1H-benzo[de]isoquinolin-6-yl)imino]methyl}-1-(2-hydroxyethyl)pyridinium bromide, 1-(2-hydroxyethyl)-4{(E)-[2-methyl-1,3-diketo-2,3-dihydro-1H-benzo[de]isoquinolin-6-yl)iminomethyl}pyridinium bromide, 1-methyl-4-{(E)-[(2-methyl-1,3-diketo-2,3-dihydro-1H-benzo[de]isoquinolin-6-yl)imino]methyl}pyridinium methylsulfate and 1-methyl-4-{(E)-[2-methyl-1,3-diketo-2,3-dihydro-1H-benzo[de]isoquinolin-6-yl)imino]methyl}quinolinium methylsulfate.

3. An agent for coloring keratin fibers, comprising at least one cationic naphthalene derivative selected from the group consisting of 4-{(E)-[(1,3-diketo-2,3-dihydro-1H-benzo[de]isoquinolin-6-yl)imino]methyl}-1-(2-hydroxyethyl)pyridinium bromide, 4-{[(E)-[2-{4-[ethyl(2-hydroxyethyl)amino]phenyl}-( 1,3-diketo-2,3-dihydro-1H-benzo[de]isoquinolin-6-yl)imino]methyl}-1-methylpyridinium methylsulfate, 1-(2-hydroxyethyl)-4-{(E)-(2-methyl-1,3-diketo-2,3-dihydro-1H-benzo[de]isoquinolin-6-yl)iminomethyl}pyridinium bromide, 1-methyl-4-{(E)-[(2-methyl-1,3-diketo-2,3-dihydro-1H-benzo[de]isoquinolin-6-yl)imino]methyl}pyridinium methylsulfate, 1-methyl-4-{(E)-[(2-methyl-1,3-diketo-2,3-dihydro-1H-benzo[de]isoquinolin-6-yl)imino]methyl}quinolinium methylsulfate, 4-[(E)-({2-[2-hydroxy-1-(hydroxymethyl)ethyl]-1,3-diketo-2,3-dihydro-1H-benzo[de]isoquinolin-6-yl}imino)methylpyridinium methylsulfate, 4-((E)-{[2-(3,4-dichlorophenyl)-1,3-diketo-2,3-dihydro-1H-benzo[de]isoquinolin-6-y]imino}methyl)-1-(2-hydroxyethyl)pyridinium bromide, and 2-[(E)-({2-[2-hydroxy-1-(hydroxymethyl)ethyl]-1,3-diketo-2,3-dihydro-1H-benzo[de]isoquinolin-6-yl}imino)methyl]-3-methyl-1,3-thiazol-3-ium methylsulfate.

4. An agent for brightening and coloring keratin fibers, comprising at least one cationic naphthalene derivative selected from the group consisting of 4-{(E)-[(1,3-diketo-2,3-dihydro-1H-benzo[de]isoquinolin-6-yl)imino]methyl}-1-(2-hydroxyethyl)pyridinium bromide, 4-{[(E)-[2-{4-[ethyl(2-hydroxyethyl)amino]phenyl}-(1,3-diketo-2,3-dihydro-1H-benzo[de]isoquinolin-6-yl)imino]methyl}-1-methylpyridinium methylsulfate, 1-(2-hydroxyethyl)-4-{(E)-(2-methyl-1,3-diketo-2,3-dihydro-1H-benzo[de]isoquinolin-6-yl)iminomethyl}pyridinium bromide, 1-methyl-4-{(E)-[(2-methyl-1,3-diketo-2,3-dihydro-1H-benzo[de]isoquinolin-6-yl)imino]methyl}pyridinium methylsulfate, 1-methyl-4-{(E)-[(2-methyl-1,3-diketo-2,3-dihydro-1H-benzo[de]isoquinolin-6-yl)imino]methyl}quinolinium methylsulfate, 4-[(E)-({2-[2-hydroxy-1-(hydroxymethyl)ethyl-1,3-diketo-2,3-dihydro-1H-benzo[de]isoquinolin-6-yl}imino)methylpyridinium methylsulfate, 4-((E)-}[2-(3,4-dichlorophenyl)-1,3-diketo-2,3-dihydro-1H-benzo[de]isoquinolin-6-yl]imino}methyl)-1-(2-hydroxyethyl)pyridinium bromide, and 2-[(E)-({2-[2-hydroxy-1-(hydroxymethyl)ethyl]-1,3-diketo-2,3-dihydro-1H-benzo[de]isoquinolin-6-yl}imino)methyl]-1,3-methyl-1,3-thiazol-3-ium methylsulfate.

5. The agent as defined in claim 3, wherein the agent contains the cationic naphthalene derivative in an amount from 0.01 to 10 weight percent.

6. The agent as defined in claim 3, further comprising at least one synthetic polymer or a modified polymer of natural origin commonly used in cosmetic agents.

7. The agent as defined in claim 6, wherein the agent contains the polymer in an amount from 1 to 5 weight percent.

8. The agent as defined in claim 3, wherein the agent is a hair colorant.

9. The agent as defined in claim 4, wherein the agent contains the cationic naphthalene derivative in an amount from 0.01 to 10 weight percent.

10. The agent as defined in claim 4, and further comprising at least one synthetic polymer or a modified polymer of natural origin commonly used in cosmetic agents.

11. The agent as defined in claim 10, wherein the agent contains the polymer in an amount from 1 to 5 weight percent.

* * * * *